(12) United States Patent
Marchal et al.

(10) Patent No.: US 9,181,116 B2
(45) Date of Patent: Nov. 10, 2015

(54) ORGANOPHOSPHORUS DERIVATIVES AND USE THEREOF AS UNCOUPLING AGENTS

(75) Inventors: Philippe Marchal, Saint-Genis (FR); Vincent Schanen, Lyons (FR); Stephane Carret-Troncy, Grenay (FR); Mickael Berard, Grigny (FR); Luc Louvel, Lyons (FR); Agnes Pilas-Begue, Miribel (FR)

(73) Assignee: RHODIA OPERATIONS, Aubervilliers (FR)

( * ) Notice: Subject to any disclaimer, the term of this patent is extended or adjusted under 35 U.S.C. 154(b) by 763 days.

(21) Appl. No.: 13/497,133

(22) PCT Filed: Sep. 8, 2010

(86) PCT No.: PCT/EP2010/063140
§ 371 (c)(1),
(2), (4) Date: Jun. 1, 2012

(87) PCT Pub. No.: WO2011/036052
PCT Pub. Date: Mar. 31, 2011

(65) Prior Publication Data
US 2012/0238527 A1    Sep. 20, 2012

(30) Foreign Application Priority Data
Sep. 22, 2009  (FR) .................................. 09 04510

(51) Int. Cl.
*A01N 57/26* (2006.01)
*C02F 3/00* (2006.01)
*A01N 57/20* (2006.01)
*C07F 9/50* (2006.01)
*C07F 9/54* (2006.01)

(52) U.S. Cl.
CPC ................ *C02F 3/006* (2013.01); *A01N 57/20* (2013.01); *C07F 9/5004* (2013.01); *C07F 9/5407* (2013.01); *C02F 2209/001* (2013.01); *C02F 2209/36* (2013.01)

(58) Field of Classification Search
CPC ....................................................... A01N 57/26
USPC ........................................................... 514/77
See application file for complete search history.

(56) References Cited

U.S. PATENT DOCUMENTS 2,937,207  A    5/1960  Reuter et al.

FOREIGN PATENT DOCUMENTS

EP           0380359  A1    8/1990

*Primary Examiner* — San-Ming Hui
(74) *Attorney, Agent, or Firm* — Dowell & Dowell, PC

(57) ABSTRACT

The present invention relates to an organophosphonium derivative of the mean general formula (1), where n is a number comprised between 4 and 20, preferably between 5 and 10, m is a number between 0 and 10, preferably between 0 and 1, and Y is an anion.
The invention also relates to a method for preparing same, and to a method for controlling the growth of bacterial biomass in an aqueous system, including adding to said aqueous system or contacting said aqueous system with an efficient amount of an uncoupling agent selected from an organophosphonium derivative as defined above.

14 Claims, No Drawings

ORGANOPHOSPHORUS DERIVATIVES AND USE THEREOF AS UNCOUPLING AGENTS

BACKGROUND OF THE INVENTON

1. Field of the Invention

The invention relates to organophosphonium derivatives, to their preparation method and to their use as uncoupling agents. The invention relates to these uncoupling agents with view to use within the scope of control of bacterial biomass in aqueous systems, in particular in a waste water treatment plant, as well as to the use of these agents and to a method for using these agents. The uncoupling activity of a molecule consists in acting on the bacterial cell energetics so as to reduce the biomass production of waste waters while keeping the purifying activity of the bacterial cell by biological degradation of organic molecules. The details of the biochemistry and of the mechanisms involved in the respiration of cells are for example discussed in the publication "Biochemistry", $3^{rd}$ edition, author: Lubert Stryer, editor: W. H. Freemen & Company, New York, USA, 1998 and also in the publication "General Microbiology", $3^{rd}$ edition, authors: Roger Y. Stanier, Michael Doudoroff and Edward A. Adelberg, editor: Macmillan, 1971.

2. Description of the Related Art

The uncoupling activity of a molecule on bacterial growth is in fine expressed by overconsumption of oxygen induced by unbalance of the bacterial energetics.

This uncoupling activity of a molecule is of interest for an application in a waste water treatment plant, designated subsequently by the French abbreviation STEP, in the case when it allows significant reduction at the source of the production of activated sludges.

The production of biomass and therefore of activated sludges in the treatment of waste waters, originates from the consumption of nutrients in the waste waters. By a respiratory process, the nutrients are oxidized and this releases energy which may be used by micro-organisms within the scope of cell division. Now, the consumption of nutrients induces a flow of protons at the bacterial membrane by the phenomenon of oxidative phosphorylation; this flow will establish a proton gradient which itself operates proton pumps which allow synthesis of ATP (Adenosine TriPhosphate) from ADP+P. ATP provides energy to the cell during cell processes (including cell division).

If this energy release could be avoided, this would lead to a decrease in biomass generation by inhibiting energy production. The uncoupling corresponds to the inhibition of the formation of energy supplies in the form of ATP. An uncoupling agent reduces the energetic yield of the combustion of carbon while increasing the proportion of carbon oxidized into $CO_2$. The uncoupling is therefore expressed by less production of biomass and by greater consumption of oxygen.

The bacterial biomass produced during waste water treatment is expensive to remove and therefore a decrease in the biomass leads to a reduction in the costs of removal.

BRIEF SUMMARY OF THE INVENTION

An aim of the present invention is to propose uncoupling molecules, for which the efficiency is measured by a drop in the production of biological sludges at the source, i.e. in aeration tanks of urban waste water treatment plants, by at least 30%.

Another object of the present invention is to propose uncoupling molecules, for which the efficiency is substantially equivalent, or even greater than that of the reference molecule THPS (Tetrakis Hydroxymethyl Phosphonium), the efficiency of which on the reduction of biological sludge production has been shown in patent application WO 2004/113236.

Another object of the present invention is to propose alternative uncoupling molecules to THPS, for which abiotic and biotic degradability is less rapid than that of THPS without however, said molecules be non-degradable which would pose environment issues.

DETAILED DESCRIPTION OF THE INVENTION

Finally, another object of the present invention is to propose uncoupling molecules, for which the toxicological and ecotoxicological profile is satisfactory and adequate for the use of the latter in STEP.

These objectives and other ones are achieved by the present invention which indeed relates to an organophosphonium derivative of the average general formula (1):

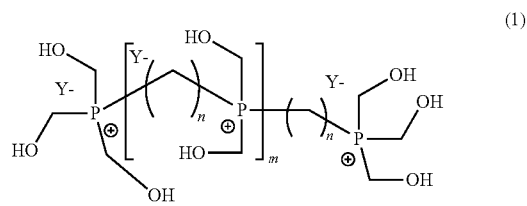

(1)

wherein:

n is a number comprised between 4 and 20 preferably between 5 and 10, m is a number comprised between 0 and 10, preferably between 0 and 1, and Y is an anion, preferably a chloride, sulfate, phosphate or bromide anion.

For the preferred compounds of the invention, n is comprised between 5 and 10, m is 0 or 1; and Y is a chloride, sulfate, phosphate or bromide anion.

For still further preferred compounds of the invention, n is 8 and m is 0 or 1.

The present invention also relates to a method for preparing an organophosphonium derivative as defined above, comprising the following steps:

a) tetrakis(hydromethyl)phosphonium chloride is reacted on a strong base such as soda, under an inert atmosphere in order to obtain trishydroxymethyl phosphine with removal of formaldehyde according to the reaction scheme below:

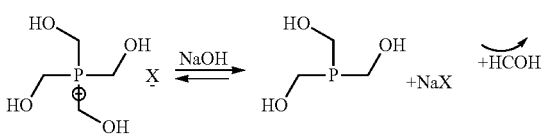

wherein x represents an anion;

b) an alpha, omega, dihalogeno-alkylene is reacted on the reaction mass obtained in Example a), and the corresponding alkylene diphosphonium is obtained.

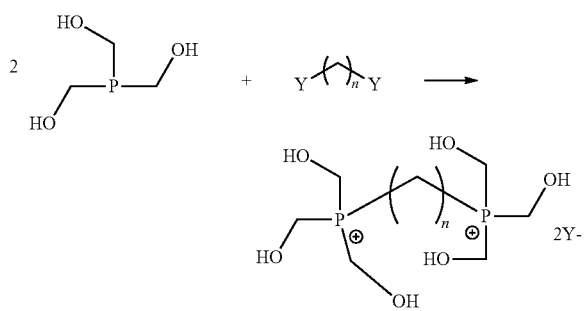

c) optionally the alkylene diphosphonium obtained in step b) reacts on an excess of dihalogeno-alkylene and of trishydroxymethyl phosphine in order to give a tri- or poly-phosphonium with release of formaldehyde according to the reaction scheme above:

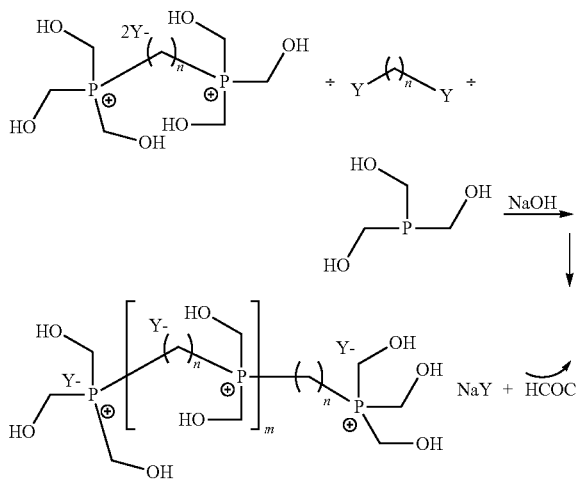

X, Y, n and m have the meaning given for formula (1) above.

The present invention is also directed to a method for controlling the growth of the bacterial biomass in an aqueous system comprising adding to the aqueous system, or contacting with the aqueous system, an effective amount of an uncoupling agent selected from an organophosphonium derivative of the average general formula (1):

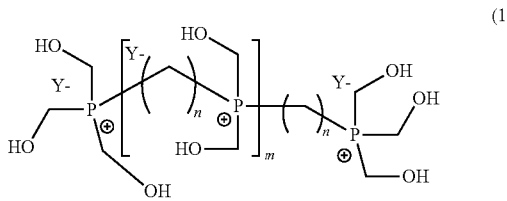

wherein:
n is a number comprised between 4 and 20, preferably between 5 and 10,
m is a number, comprised between 0 and 10, preferably between 0 and 1, and
Y is an anion, preferably selected from the group constituted by chloride, sulfate, phosphate, acetate and bromide ions.

Still more preferably n is 8 and m is 0 or 1.

The invention is also directed to a method for controlling the growth of bacterial biomass in an aqueous system comprising adding to the aqueous system, or contacting with the aqueous system, an effective amount of an uncoupling agent selected from an organophosphonium derivative as defined above.

The effective amount of organophosphonium derivative added to the aqueous system can represent up to 100 mg/l, for example up to 50 mg/l, such as up to 30 mg/l. Preferably, the effective amount of organophosphonium derivative added to the aqueous system represents from 0.0001 mg/l to 100 mg/l, from 0.005 mg/l to 50 mg/l, for example from 0.01 mg/l to 30 mg/l, such as from 0.05 mg/l to 10 mg/l. More preferably, the effective amount of organophosphonium derivative represents from 0.1 to 10 mg/l, for example from 0.5 mg/l to 7.5 mg/l, such as from 1 to 5 mg/l.

The organophosphonium derivative in the uncoupling agent application may be formulated with one or more of the following chemicals conventionally used in the treatment of waste waters:
a surfactant;
an anti-foam agent;
a scale inhibitor;
a corrosion inhibitor;
a biocide;
a flocculant;
an agent facilitating solid/water separation; and
a dispersant.

Preferably, the aqueous system will be a waste water treatment plant which is used for treating industrial or municipal effluents. This installation recovers waste waters from industrial processes (for example, paper production, food industry, chemical industry) and/or from dwellings and institutional buildings and similar installations, by using micro-organisms in aerobic, anoxic processes (for example denitrification), for consuming organic pollutants and making the water suitable with view to its reuse or its discarding into the environment.

The present invention therefore provides a method for controlling the growth of bacterial biomass in an aqueous system comprising adding to, or contacting with, the aqueous system, an effective amount of an uncoupling agent as defined above.

In a preferred embodiment, the present invention provides a method for controlling the growth of bacterial biomass in an aqueous system, which method comprises contacting an effective amount of an uncoupling agent as defined above directly with the bacterial biomass. In order to apply this method, it is recommended to put within a limited time a maximum volume of activated sludge into contact with the uncoupling agent so as to obtain optimum efficiency from the latter.

Thus, for biological pilot tests in the laboratory, the direct contact of the uncoupling agent in water with the bacterial biomass is designated by the expression "instantaneous dosage" or "instantaneous mixing" called flash mixing.

It was discovered that if the uncoupling agent is simply added directly to a bioreactor containing sludges, then the efficiency of the agent is substantially decreased since the uncoupling agent is capable of interacting with the other materials present in the bioreactor and the action of the organophosphonium derivative is substantially reduced.

Moreover, the effective amount of said organophosphonium derivative may represent from 0.1 to 100 mg per gram of solids (expressed as dry materials or DM) present in the sludges in the aqueous system, preferably from 0.5 to 100 mg/g for example from 1 to 50 mg/g, such as from 2 to 10 mg/g.

The following examples illustrate the invention without limiting the scope thereof.

EXAMPLE 1

Step a) Synthesis of a Trishydroxymethyl Phosphine Solution

In a perfectly stirred reactor equipped for vacuum distillation, inertized beforehand under nitrogen, is loaded:
a solution titrating 80% THPC (tetrakis(hydromethyl) phosphonium chloride) and containing 150 g of THPC (0.63 mol);
the mixture is cooled to 5-15° C.;
385 g of an 8% soda solution are poured within 3 hours and with control of the temperature at 5-15° C.;
at the end of the pouring, the reaction mixture is maintained at 10° C. for 12 hours;
the formaldehyde formed is removed by distillation of a water/formaldehyde mixture at a temperature of 15-30° C. and at a pressure <10 mbars;
970 g of ethanol are added and distillation is performed under the same conditions in order to use up the formaldehyde;
precipitation of NaCl is observed and after distillation the reaction mass is analyzed:
Analyses: 93.5% of THP/3% THPO/3.5% THPC

EXAMPLE 2

Steps b) and c): Synthesis of Phosphonium (Formula (1) with n=8, m=0 or 1)

The reaction mass prepared in Example 1 is introduced into a perfectly stirred reactor equipped for vacuum distillation, inertized beforehand.
While controlling the temperature at 45-55° C., 111.8 g of 1,8-di-iodoctane are poured within 30 minutes.
The reaction medium is biphasic and precipitation of salts is observed (NaI/NaCl).
After being maintained at 50° C. for 50 hours, the reaction medium is filtered and the obtained product is a pale yellow limpid solution from which a mass of 665 g is extracted having the following NMR analysis (nuclear magnetic resonance):
$^{31}$P NMR analysis
3% THPO
3% THP
14% THPC
78% of phosphonium derivatives according to a following molar composition of the di-phosphonium and tri-phosphonium:

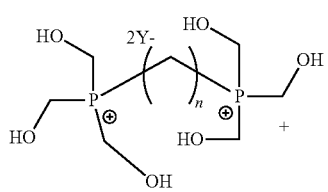

n=8
87%

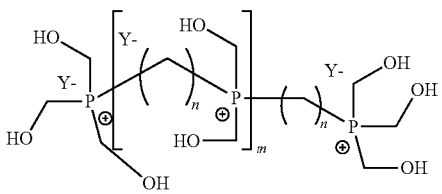

n=8
13%

EXAMPLE 3

Step a) Synthesis of a Trishydroxymethyl Phosphine Solution:

In a perfectly stirred reactor, equipped for vacuum distillation, inertized beforehand under nitrogen, a solution titrating 80% THPC (tetrakis(hydromethyl)phosphonium chloride) with 100 g of THPC (0.42 mol) and water (50 g) is loaded;
The mixture is cooled to 5-15° C.;
228 g of the 8% soda NaOH solution are poured within 3 hours and with control of the temperature at 5-15° C.;
At the end of the pouring, 10° C. is maintained for 12 hours;
The formaldehyde formed is removed by distillation of a water/formaldehyde mixture at a temperature of 15-30° C. and at a pressure of less than 10 mbars;
786 g of ethanol are added and the reaction mixture is distilled under the same conditions in order to use up the formaldehyde;
Precipitation of NaCl is observed.

EXAMPLE 4

Steps b) and c): Synthesis of Phosphonium (Formula (1) with n=6, m=0 or 1)

The reaction mass prepared in Example 3 is introduced into a perfectly stirred reactor equipped for vacuum distillation, inertized beforehand, with control of the temperature at 45-55° C.;
111.8 g of 1,6-diiodohexane are poured with 30 minutes and the temperature is controlled at 45-55° C.;
The obtained reaction medium is biphasic and precipitation of salts is observed (NaI/NaCl);
The temperature of the reaction mixture is maintained at 50° C. for 30 hours with presence of 15% THPC;
At a temperature of 10° C., 30 g of 8% NaOH are added;
The temperature is set to 40° C.;
14.5 g of 1,6-diiodohexane are poured in;
The reaction medium is maintained at 50° C. for 12 hours;
The reaction mixture is cooled to 10° C., and then filtered on a frit of porosity 3;
The formaldehyde formed is removed by distillation of a water/formaldehyde mixture at a temperature of 15-30° C. and at a pressure <10 mbars; and
400 g of ethanol are added and distilled under the same conditions in order to use up the formaldehyde.
At a temperature of 10° C., 15 g of 8% NaOH are added;
Temperature is set to 40%;
10 g of 1,6-diiodohexane are poured in while maintaining the reaction mixture at 50° C. for 12 hours;
The reaction medium is cooled to 10° C. and then filtered on a frit of porosity 3;

The formaldehyde formed is removed by distillation of a water/formaldehyde mixture at a temperature of 15-30° C. and at a pressure <10 mbars; and then 350 g of water are added and distilled under the same conditions in order to use up the formaldehyde;

The obtained product is a pale yellow limpid solution from which a mass of 327.7 g is drawn off;

The drawn-off aqueous phase is washed with 3 washings with ethyl acetate (AcOEt 350 g)

The washed aqueous phase is desolvated in the rotary evaporator and 284 g of a pale yellow solution are obtained, having the following nuclear magnetic resonance analysis:

$^{31}$P NMR analysis
1.6% THPO
3% THPC

The method and the apparatus used are those described in Example 3 of WO 2004/113236 cited as a reference. The strain *Schinella granuli* was used as an inoculum in this methodology (which differs from Example 3 of WO 2004/113236 which used activated sludge).

The obtained results in the screening test are gathered in Table 1 below. They are expressed as an uncoupling percentage relatively to the control (not comprising any uncoupling agent). This means that for Ex2 at 0.05 mg/l, we have an oxygen overconsumption of 18% relatively to the control not comprising any uncoupling agent. THPS (tetrakis(hydromethyl)phosphonium sulfate) produces uncoupling effects in the oxitop® respirometry tests of 16±8% for a rated concentration of 3 ppm, the 95% confidence interval of THPS in terms of uncoupling factor being [10-22], values computed from results obtained in 26 Oxitop® tests.

TABLE 1

| Product | Concentration in ppm | | | | | | | |
|---------|------|------|------|------|------|------|------|------|
|         | 0.05 | 0.1  | 0.5  | 1    | 2    | 3    | 4    | 5    |
| Ex. 2   | 18%  | 12%-16% | 15%-8%-14% | 15%-16%-15% | 10%-9% | —    | —    | —    |
| THPS    |      |      |      |      |      | 16 ± 8% |   |   |

95% phosphonium derivatives of composition:

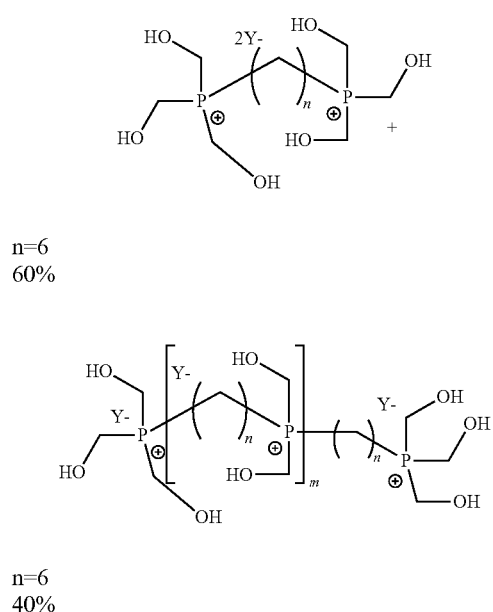

n=6
60% n=6
40%

EXAMPLE 5

Detecting the Reduction of Activated Sludge by an Organophosphonium Derivative in an Oxytop® Screening Test:

In order to evaluate the reduction in sludge production by an uncoupling chemical agent in respirometry (in order to measure oxygen overconsumption, a characteristic signature of the effects of an uncoupling agent), the oxytop® test technique is used containing a synthetic medium and bacterial strains particularly sensitive to uncoupling agents. These model bacterial strains (notably the strain *Schinella granule*) are particularly representative of activated sludges of STEP since they are isolated from the latter in aeration tanks.

A rather narrow concentration range in which these derivatives show good efficiency is observed on the phosphonium derivatives synthesized in Example 2.

This concentration range often shows activation of the decoupling effect at low concentrations followed by a slight inhibition and then toxicity obtained around 5 ppm (rated concentration).

Uncoupling effects are observed of the same order of magnitude as the ones obtained with THPS (16±8%, average value obtained over 26 Oxitop® tests with 3 ppm of THPS). The mixture of triphosphonium and diphosphonium of Example 2. gives repeatable and significant uncoupling effects on the relatively low concentration range comprised between 0.1 and 2 ppm. The optimum concentration seems to be located at 1 ppm with effects of the order of 15%.

EXAMPLE 6

Detection of the reduction of activated sludge by an organophosphonium derivative in a Chemostat® biological pilot.

Tests on biological pilots continuously fed with synthetic effluent dealt with the molecule of Ex2 (Example 2 above), show significant uncoupling effects on the reduction of sludge production. The biological pilots have a volume of 5 liters and are continuously aerated; a purge of the latter is made everyday (except on weekends) in order to obtain a sludge age of about 7 days. The biological pilots were seeded with activated sludge from the urban STEP of St-Fons (France). After a short acclimatization period of the sludge, the treatment with the molecule Ex2 was carried out according to the flash mixing method also described in Example 1 of WO 2004/113236 cited as a reference.

An experiment, for which the total period of injection of the uncoupling product according to the flash mixing method lasted for 3 months, gave the following results:

| Treatment | Reduction in sludge production | Growth rate (in g of MLSS/g of removed COD) | Reduction in growth rate |
| --- | --- | --- | --- |
| Control (untreated) | / | 0.188 | / |
| THPS 2.9 ppm | 13.6% | 0.171 | 9.0% |
| Compound Ex2, 1.1 ppm | 14.9% | 0.182 | 3.2% |
| Compound Ex2, 2.3 ppm | 20.2% | 0.160 | 14.9% |

Good efficiency of the compound Ex2 on the reduction of sludge production, notably at 2.3 ppm, is observed with a reduction slightly greater than 20% in comparison with the untreated control.

A complementary experiment, this time using two different grades of the compound Ex2 of Example 2 above, designated as EX21 and EX22a hereafter, gave the following results over a 1 month injection period:

| Treatment | Reduction in sludge production | Growth rate (in g of MLSS/g of removed COD) | Reduction in the growth rate |
| --- | --- | --- | --- |
| Control (untreated) | / | 0.174 | / |
| Compound EX21, 2.3 ppm | 37.4% | 0.113 | 35.1% |
| Compound EX22, 2.3 ppm | 24.3% | 0.135 | 22.5% |
| Compound EX22, 5.7 ppm | 27.6% | 0.129 | 26.0% |

Compound EX22 shows good efficiency on the reduction of sludge production of 27.6% and a reduction in the growth rate of 26% (which confirms that at this concentration, it does not alter the purifying capacity of sludges).

The invention claimed is:

1. A method for controlling growth of bacterial biomass in an aqueous system comprising adding to the aqueous system or contacting with the aqueous system, an uncoupling agent selected from an organophosphonium derivative of the average general formula (1):

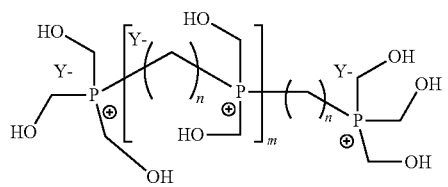
(1)

Wherein:
n is a number comprised between 4 and 20,
m is a number comprised between 0 and 10, and
Y is an anion.

2. The method according to claim 1, wherein the uncoupling agent is present in an amount between 0.001 and 100 mg/l.

3. The method according to claim 2, wherein the uncoupling agent is present in an amount between 0.005 and 50 mg/l.

4. The method according to claim 3, wherein the uncoupling agent is present in an amount between 0.01 mg/l to 30 mg/l.

5. The method according to claim 4, wherein the uncoupling agent is present in an amount between 0.1 mg/l to 10 mg/l.

6. The method according to claim 5, wherein the uncoupling agent is present in an amount between 0.5 mg/l to 7.5 mg/l.

7. The method according to claim 6 wherein the uncoupling agent is present in an amount between 1 mg/l to 5 mg/l.

8. The method according to claim 1, wherein the uncoupling agent is present in an amount between 0.1 mg to 100 mg per g of solids, expressed as dry material, present in sludges in the aqueous system.

9. The method according to claim 8, wherein the uncoupling agent is present in an amount between 1 mg to 50 mg per g of solids present in the sludges in the aqueous system.

10. The method according to claim 9, wherein the uncoupling agent is present in an amount between 2 mg to 10 mg per g of solids present in the sludges in the aqueous system.

11. The method according to claim 1, wherein the aqueous system is a waste water treatment plant for treating industrial or municipal effluents.

12. A method for preparing an organophosphonium derivative of the average general formula (1):

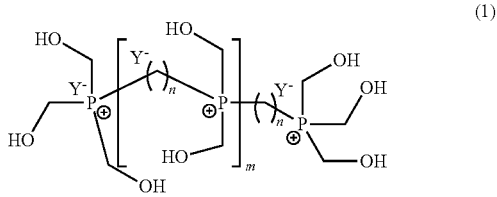
(1)

Wherein:
n is a number comprised between 4 and 20,
m is a number comprised between 0 and 10, and
Y is an anion, comprising the following steps:
a) tetrakis(hydromethyl)phosphonium chloride is reacted on a strong base like soda, under an inert atmosphere in order to obtain trishydroxymethyl phosphine with removal of formaldehyde according to the reaction scheme below:

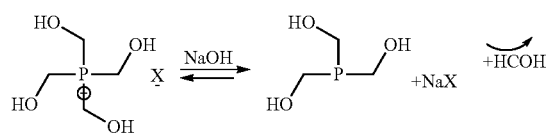

wherein x represents an anion;
b) an alpha, omega, dihalogeno-alkylene is reacted on the reaction mass obtained in Example a) and the corresponding alkylene diphosphonium is obtained

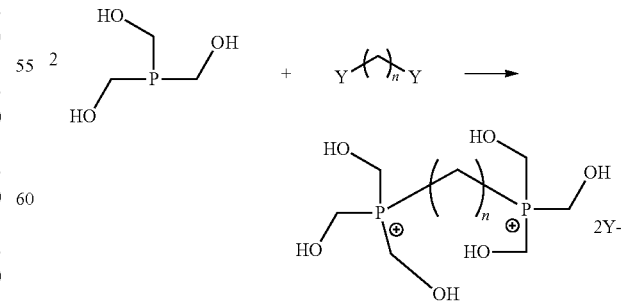

c) optionally the alkylene diphosphonium obtained in step b) reacts on an excess of dihalogeno alkylene and of trishydroxymethyl phosphine in order to give tri or polyphosphonium with release of formaldehyde according to the reaction scheme above:

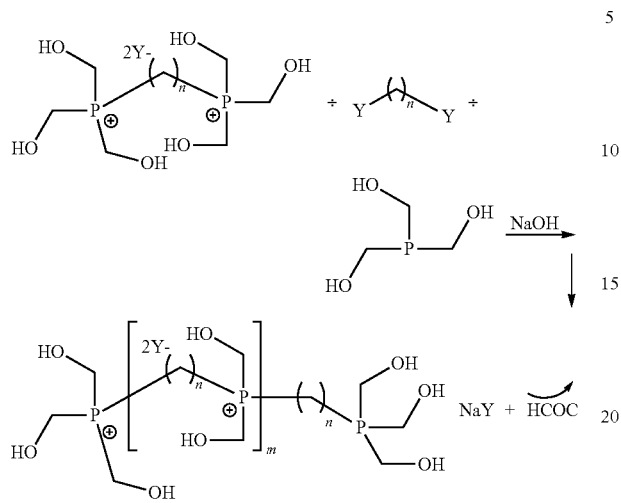

X, Y, n and m having the meaning given in formula (1) above.

13. The method of claim 1 wherein n is comprised between 5 and 10, m is 0 or 1, and Y is an anion selected from a group of anions consisting of chloride, sulfate, phosphate or bromide anions.

14. The method of claim 1 wherein n is 8 and m is 0 or 1.

* * * * *